United States Patent [19]

Ye

[11] Patent Number: 5,742,525
[45] Date of Patent: Apr. 21, 1998

[54] METHOD FOR ELIMINATING THE FLUCTUATION AND DRIFT OF SPECTRAL LINE INTENSITIES

[76] Inventor: Yuancai Ye, 27B Martin St., Clemson, S.C. 29631

[21] Appl. No.: 370,988

[22] Filed: Jan. 10, 1995

[51] Int. Cl.$^6$ .................................................. G01V 13/00
[52] U.S. Cl. ............... 364/571.02; 364/498; 364/571.01; 364/571.04; 356/306; 356/319; 356/326; 250/252.1 A; 250/339.07; 250/252.1 R
[58] Field of Search .................................... 364/498, 574, 364/497, 571.01, 571.02, 571.04, 525, 526; 356/306, 308, 319, 346, 325, 326; 250/252.1 A, 252.1 R, 334.07–334.09; 73/1 R, 23, 36, 37; 324/307

[56] References Cited

U.S. PATENT DOCUMENTS

| | | | |
|---|---|---|---|
| 4,875,169 | 10/1989 | Synovec et al. | 364/497 |
| 4,893,259 | 1/1990 | Grosser et al. | 356/326 |
| 5,121,337 | 6/1992 | Brown | 364/498 |
| 5,311,444 | 5/1994 | Ohta | 364/497 |
| 5,397,899 | 3/1995 | DiFoggio et al. | 364/498 |

*Primary Examiner*—Emanuel T. Voeltz
*Assistant Examiner*—Hal D. Wachsman

[57] ABSTRACT

This invention is a method for improving the quality of analytical measurement data by eliminating the fluctuation and drift of spectral line intensities obtained by an atomic emission spectrometer or a mass spectrometer. Carrying out this method needs measuring intensities of an analytical line and two reference lines for a sample. This method is involved in the calculation of a sequence of analytical line intensity ratios $I_j$ and a sequence of fluctuation disagreements $F_j$ of intensities between two reference lines, in the use of one of the following three equations $$I_j = K_0 + K_1 C_j + K_{fl} C_j F_j$$

$$I_j = K_0 + K_1 C_j + K_{fl} C_j F_j + K_{t1} C_j T_j$$

$$I_j = K_0 + K_1 C_j + K_{fl} C_j F_j + K_{t1} C_j T_j + K_{t2} C_j T_j^2$$

to regress out a relationship among the ratios, fluctuation disagreements, times $T_j$ and concentrations $C_j$ using a sequence of standard samples where $K_0$, $K_1$, $K_{fl}$, $K_{t1}$ and $K_{t2}$ are coefficients to be regressed out, and finally in the prediction of a component concentration for an unknown sample according to one of the above three equations previously used for the regression.

4 Claims, 1 Drawing Sheet

METHOD FOR ELIMINATING THE FLUCTUATION AND DRIFT OF SPECTRAL LINE INTENSITIES

CROSS-REFERENCES TO RELATED APPLICATIONS

| U.S. Pat. Documents | | | |
|---|---|---|---|
| 5,121,337 | 6/1992 | Brown... | 364/498 |

OTHER PUBLICATIONS

M. H. Ramsey and M. Thompson "Improved Precision in Inductively Coupled Plasma Atomic-emission Spectrometry by a Parameter-related Internal Standard Method" *Analyst,* 109, 1625–1626, Dec. 1984.

A. Lorber and Z. Goldbart "Generalized Internal Reference Method for Simultaneous Multichannel Analysis", *Analytical Chemistzy,* 56, 37–43, Jan. 1984.

STATEMENT AS TO RIGHTS TO INVENTIONS MADE UNDER FEDERALLY SPONSORED RESEARCH AND DEVELOPMENT

I state here that this invention does not have any relationship with others else.

BACKGROUND OF THE INVENTION

(1) Field of the Invention

The present invention relates to a method for eliminating the fluctuation and drift of spectral line intensities and improving the accuracy and precision of measurement data obtained by atomic emission spectrometers or mass spectrometers with different ionization or radiation sources, and particularly by multichannel atomic emission or mass spectrometers which have more than three detectors for the measurement of spectral line intensities simultaneously.

(2) Description of the Prior Art

Many atomic emission and mass spectrometers are in use today. These spectrometers output analysts a great number of spectral line intensities always with unexpected short-term change in intensity which will be called as fluctuation and long-term change in intensity which will be defined as drift. Because a spectral line intensity always includes a relevant and hoped analytical signal superimposed with non-relevant and non-hoped fluctuation and drift, many times the fluctuation and drift often make it impossible for an analyst to precisely and accurately analyze a component in a sample. How to reduce the fluctuation and drift is a key way to improve the quality of a final analytical result.

Strict control of experimental environment and procedures helps to reduce the fluctuations and drifts of spectral line intensities, but it is limited and often not effective. The optimization and improvement of instrumentation are good ways to eliminate the fluctuations and drifts of intensities. However, it is almost impossible for an analyst to modify a commercial atomic emission spectrometer or mass spectrometer. Even if the analyst can do it, it needs much time and money for the improvement of the spectrometer. All the commercial manufacturers involved in producing these spectrometers in the world also try their bests to reduce the fluctuations and drifts of spectral line intensities of their spectrometers and to make them stable as much as possible, but it is still very difficult even for these manufacturers to further keep on improving their spectrometers too.

One simple and conventional method to improve the precision and accuracy of analytical results is internal reference method, which uses only one internal reference line. However, this internal reference method can only partially reduce the fluctuation and drift of obtained intensities because the fluctuation and drift characteristics of analytical line intensities are always not exactly the same as those of the used internal reference line intensities. Therefore, internal reference line intensities are always not able to completely compensate the fluctuations and drifts of analytical line intensities. Consequently, this method is often unsatisfactory to analysts.

The improvement of analytical results by a mathematical calculation method sometimes is a good and effective way to approach this purpose. Various multivariate calibration methods such as classical least square (CLS), partial least square (PLS) and principal component regression (PCR), which normally require more than one hundred (at least 5×N (N means the number of components to be analyzed.)) spectral intensities at different wavelengths, are well widely applied to different band-like molecular spectra like Ramon, mid- and near-infrared, visible and ultraviolet spectra usually with a couple of band-like peaks. One multivariate calibration calculation method is described in U.S. Pat. No. 5,121,337 by Brown for correcting spectral data from various infrared spectra. Unlike these band-like molecular spectra, atomic emission spectra or mass spectra are line-like and very narrow. Moreover, most of components or elements have too few spectral lines available for the use of the above multivariate calibration methods because weak spectral lines disappear especially when these components or elements are at a lower lever of concentrations. These characteristics of line-like spectra actually make it very difficult for analysts to apply these multivariate calibration methods to atomic emission and mass spectra. In fact, as far as I have known, No people have reported these multivariate calibration methods for the improvement of the precision and accuracy of analytical data with an atomic emission spectrometer or mass spectrometer before. A parameter related internal standard method was developed for the improvement of inductively coupled plasma atomic emission spectrometry measurement precisions by M. H. Ramsey and M. Thompson normally using three or more internal reference lines as reported in "Improved Precision in Inductively Coupled Plasma Atomic-emission Spectrometry by a Parameter-related Internal Standard Method" by M. H. Ramsey and M. Thompson, *Analyst,* 109, 1625–1626 (1984). An alternative standardization method was suggested by A. Lorber and Z. Goldbart to eliminate nonrandom fluctuations and drifts in analytical channels using five internal reference lines with a multichannel spectrometer as published in "Generalized Internal Reference Method for Simultaneous Multichannel Analysis" by A. Lorber and Z. Goldbart, *Anal. Chem.,* 56, 37–43 (1984). However, the above two methods must not only require more than two internal reference lines but also measure correlation parameters between an analytical line and every internal reference line in advance. Both methods have a problem how to measure these parameters accurately. It is also difficult to find so many reference lines without spectral interferences.

It is therefore a challenge to create a novel method which should be simple, understandable, and easy to be universally used with an atomic emission spectrometer or mass spectrometer. Besides, this method should require a little or no modification of current spectrometers. An object of the present invention is just to provide such a new calculation method for eliminating the various fluctuations and drifts of spectral line intensities to improve the precision and accuracy of final analytical results. This method, which will be detailed in the following sections of the summary of the invention and description of the preferred embodiments, only needs two internal reference lines. It is rather simple, understandable, and very applicable to all atomic emission and mass spectrometers and particularly to various multichannel spectrometers without the need of the measurement of any parameters.

SUMMARY OF THE INVENTION

This invention is developed from one simple and new idea that the fluctuation disagreements of intensities between an analytical line and a reference line has a specific connection, although this connection is unknown to an analyst, with the fluctuation disagreements of intensities between two reference lines themselves. This specific connection can be automatically obtained by the linear regression of analytical line intensities verse the fluctuation disagreements and concentrations of a component to be measured with a series of standard samples. This method can be used with an atomic emission spectrometer or a mass spectrometer which generates three sequences of intensities of an analytical line ($i_j$) and two reference lines (reference line 1 ($i_{1j}$) and reference line 2 ($i_{2j}$)) at the time j for a sample j where j could be 1, 2, 3, 4, ..., n, ... The intensity ratio $I_j$ of analytical line intensity $i_j$ to the first reference line intensity $i_{1j}$ for the sample j can be derived from the following formula (1):

$$I_j = i_j \div i_{1j} \quad (1)$$

This formula can only reduce a fraction of fluctuation between analytical line and reference line intensities because the fluctuation characteristics of analytical line intensities are not exactly the same as those of reference line intensities and the disagreements in fluctuation characteristics always exist unfortunately.

Moreover, two intensities of reference lines 1 and 2 obtained at the standard time s for the freely pre-chosen standard sample s are notified as $i_{1s}$ and $i_{2s}$, respectively. The fluctuation disagreement $F_j$ at the time j relative to the chosen standard time s between two reference lines can be obtained by computing the formula (2):

$$F_j = (i_{2j} \div i_{1j}) - (i_{2s} \div i_{1s}) \quad (2)$$

In some cases, a spectral line intensity is a function of time because the measured intensity always drifts with time. Various drifts of different line intensities have either a linear or parabolic relationship with time. These drifts can be eliminated by mathematical calculation.

Further based on the new ideas depicted in the first and third paragraphs in this section of this invention, the following equation (3), which actually states that the intensity ratio $I_j$ of analytical line intensity $i_j$ to reference line intensity $i_{1j}$ is the function of the concentration $C_j$ of a component in sample j, fluctuation disagreement $F_j$ and time $T_j$, is always true:

$$I_j = \phi(C_j, F_j, T_j) \quad (3)$$

This equation can not be directly used by an analyst, but it can be simplified into many different equations. The following three equations (4), (5) and (6), which are the simplest and probably most useful among all of them, can be induced provided that an analytical line intensity ratio $I_j$ is proportional to the corresponding concentration $C_j$ and the fluctuation disagreement between the analytical line and a reference line has a linear relationship with the fluctuation disagreement between two reference lines, $$I_j = K_0 + K_1 C_j + K_{f1} C_j F_j \quad (4)$$

$$I_j = K_0 + K_1 C_j + K_{f1} C_j F_j + K_{t1} C_j T_j \quad (5)$$

$$I_j = K_0 + K_1 C_j + K_{f1} C_j F_j + K_{t1} C_j T_j + K_{t2} C_j T_j^2 \quad (6)$$

where $K_0$, $K_1$, $K_{f1}$, $K_{t1}$ and $K_{t2}$ are coefficients which can be easily calculated out by the least square regression of intensity ratios verse the concentrations, times, and fluctuation disagreements between two reference lines for a component in a series of standard samples. These equations eliminate not only the portion of the analytical line intensity fluctuation whose characteristics are completely in accordance with the reference line intensity fluctuation characteristics but also the portion of the analytical line intensity fluctuation whose characteristics are not in agreement with the reference line intensity fluctuation characteristics and the drift in analytical line intensity.

Finally, one of the above last three equations previously employed for the regression can be used to simply and quickly predict the concentration of a component in an unknown sample as long as $K_0$, $K_1$, $K_{f1}$, $K_{t1}$ $K_{t2}$ coefficients are obtained using a series of standard samples, because the intensity ratio I and the fluctuation disagreement F can be similarly derived with the formulas (1) and (2), respectively after the analytical line intensity i and intensities of the first reference line $i_1$ and the second reference line $i_2$ for the unknown sample are output from an atomic emission spectrometer or a mass spectrometer, and time T is printed out by an employed computer with the spectrometer.

DESCRIPTION OF THE PREFERRED EMBODIMENT

Figure 1:
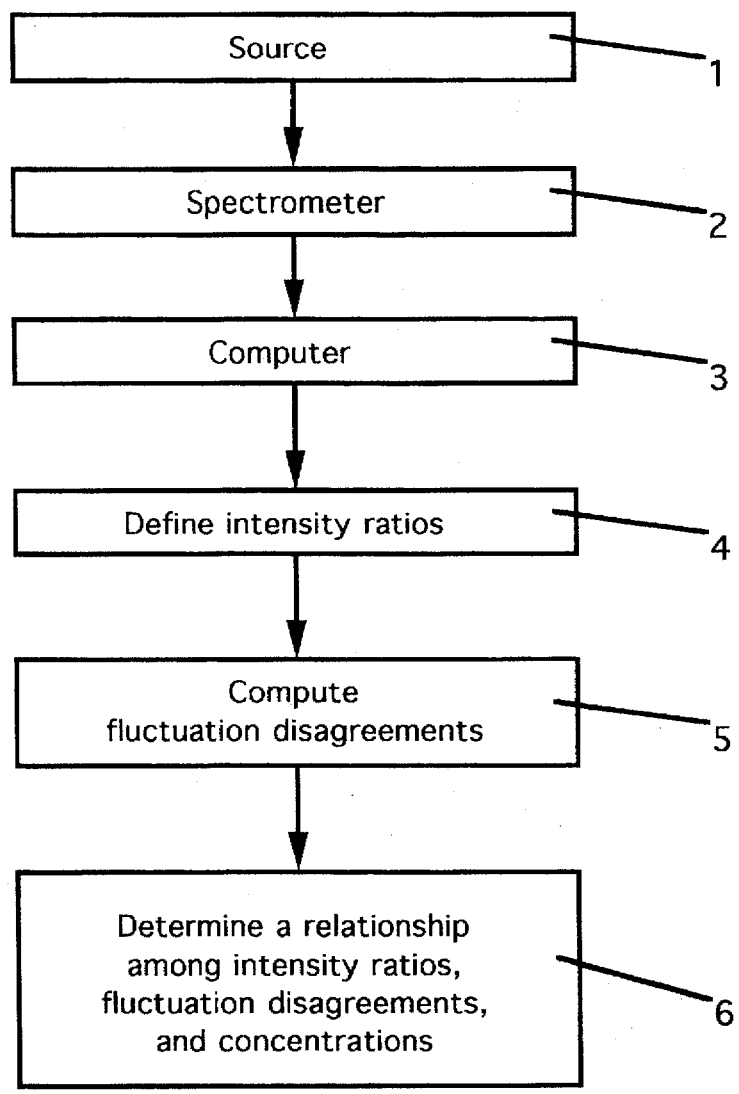
FIG. 1 graphically shows a flow chart of a program for carrying out this invention.

A flow chart of a program for carrying out this invention is shown in the block diagram of FIG. 1. The measurement system in FIG. 1 consists of three subsystems, namely, a source in the box 1 which is, but is not limited to either an radiation source for an atomic emission spectrometer or an ionization source for a mass spectrometer, a spectrometer in the box 2, but not limited to, including one or more detectors, and a computer in the box 3 for controlling the spectrometer in the box 2, acquiring spectral line intensities, outputting times, and storing and managing them.

Before a sample is put into the source in the box 1, one or two reference elements should be already in this sample. Additionally, the amounts of the reference elements in all standard and unknown samples should keep constant. Once both two reference lines and one or more analytical lines are separated by the spectrometer in the box 2 in FIG. 1 and also detected by one or more detectors in the spectrometer in the box 2, the intensities of these spectral lines and times will be collected and managed by the computer in the box 3 and stored in this computer for the later calculations.

After these intensities are obtained, first of all, the intensity ratio $I_j$ in the box 4 of an analytical line intensity $i_j$ to the first reference line intensity $i_{1j}$ which can be freely set from one of the two reference line intensities for a component in standard sample j can be derived from the formula (1).

$$I_j = i_j \div i_{1j} \tag{1}$$

where j represents one order number of a sequence of standard samples and can be any positive whole number except for zero. By using the formula (1), a sequence of the intensity ratios can be simply and quickly obtained.

Secondly, the fluctuation disagreement $F_j$ in the box 5 can be obtained by computing the formula (2)

$$F_j = (i_{2j} \div i_{1j}) - (i_{2s} \div i_{1s}) \tag{2}$$

wherein $i_{2j}$, $i_{1s}$ and $i_{2s}$ represent intensities of the second reference line for the standard sample j, the first reference line and the second reference line for the previously selected standard sample s, respectively. By using the formula (2), a sequence of fluctuation disagreements can be computed out.

Thirdly, one sequence of the obtained intensity ratios, one sequence of the obtained fluctuation disagreements, and one sequence of the known concentrations of a component in one sequence of standard samples can be used to generate the following equation (3) in the box 6 by the least square regression of the three sequences of data providing that the equation (3) does exist.

$$I_j = K_0 + K_1 C_j + K_{fl} C_j F_j \tag{3}$$

wherein the concentration $C_j$ is the concentration of a component in standard sample j, and $K_0$, $K_1$ and $K_{fl}$ are coefficients to be regressed out. These coefficients should be stored in the computer in the box 3 later for the prediction of a component in an unknown sample. This regression calculation can be found in many text books, and is purely a mathematical algorithm. If the drift of an analytical line intensity is needed to be eliminated and the drift is linear with time, similarly the following equation (4) in the box 6 should be used to regress $$I_j = K_0 + K_1 C_j + K_{fl} C_j F_j + K_{T1} C_j T_j \tag{4}$$

out $K_0$, $K_1$, $K_{fl}$, $K_{t1}$ coefficients they are and stored in the computer in the box 3 later for the prediction of a component in an unknown sample. If the drift of an analytical line intensity is needed to be eliminated and the drift is parabolic with time, similarly the following equation (3) in the box 6 should be used to regress $$I_j = K_0 + K_1 C_j + K_{fl} C_j F_j + K_{t1} C_j T_j + K_{t2} C_j T_j^2 \tag{5}$$

out $K_0$, $K_1$, $K_{fl}$, $K_{t1}$, $K_{t2}$ coefficients they are and stored in the computer in the box 3 later for the prediction of a component in an unknown sample.

The last step is to predict a concentration of a component in an unknown sample. Just as detailed in the first step, the intensity ratio I for this unknown sample can be obtained according to the following formula (6), $$I = i \div i_1 \tag{6}$$

where i and $i_1$ are analytical line and the first reference line intensities, respectively for the unknown sample. Again just as detailed in the second step, the fluctuation disagreement F between two reference lines for the unknown sample can be similarly derived from the following formula (7), $$F = (i_2 \div i_1) - (i_{2s} \div i_{1s}) \tag{7}$$

where $i_2$ is the second reference line intensity for the unknown sample. If the equation (3) is previously used to regress out the $K_0$, $K_1$ and $K_{fl}$ coefficients by using a sequence of standard samples in the above first three steps, the concentration C of this component in the unknown sample should be extracted according to the following formula (8).

$$C = (I - K_0) \div (K_1 + K_{fl} F) \tag{8}$$

If the equation (4) is previously used to regress out the $K_0$, $K_1$, $K_{fl}$ and $K_{t1}$ coefficients by using a sequence of standard samples in the above first three steps, the concentration C of this component in the unknown sample should be extracted according to the following formula (9)

$$C = (I - K_0) \div (K_1 + K_{fl} F + K_{t1} T) \tag{9}$$

wherein T is the time when analytical and reference line intensities are measured by an atomic emission or a mass spectrometer. If the equation (5) is previously used to regress out the $K_0$, $K_1$, $K_{fl}$, $K_{t1}$ and $K_{t2}$ coefficients by using a sequence of standard samples in the above first three steps, the concentration C of this component in the unknown sample should be extracted according to the following formula (10)

$$C = (I - K_0) \div (K_1 + K_{fl} F + K_{t1} T + K_{t2} T^2) \tag{10}$$

wherein T is the time when analytical and reference line intensities are measured by an atomic emission or a mass spectrometer.

What is claimed is:

1. A method of eliminating the fluctuation and drift of spectral line intensities with an atomic emission spectrometer or a mass spectrometer including:

measuring the intensities of two reference lines and an analytical line for a component in a standard sample j;

correspondingly outputting a time $T_j$ indicating when said standard sample j is measured with a computer which is used to control this spectrometer and store all the measured intensities;

defining an intensity ratio $I_j$ of an analytical line intensity $i_j$ to the first reference line intensity $i_{1j}$ which can be freely set from one of intensities of two reference lines for said component in said standard sample j by the following formula;

$$I_j = i_j \div i_{1j}$$

repeating the above measuring, outputting and defining steps until a sequence of standard samples known with a sequence of concentrations $C_j$ are finished to obtain correspondingly a sequence of intensity ratios and a sequence of times wherein j represents one order number of said sequence of standard samples and can be any positive whole number except for zero;

selecting one standard sample s from said sequence of standard samples;

computing a fluctuation disagreement $F_j$ of intensities between said two reference spectral lines by the following formula $$F_j = (i_{2j} \div i_{1j}) - (i_{2s} \div i_{1s})$$

wherein $i_{1j}$ and $i_{2j}$ are the first and second reference spectral line intensities, respectively measured for the standard sample j, and $i_{1s}$ and $i_{2s}$ are said first and second reference line intensities, respectively obtained for said selected standard sample s;

repeating the above computing step until a sequence of fluctuation disagreements are obtained correspondingly for said sequence of standard samples; and using one of the following three equations to regress out a relationship among said sequence of intensity ratios, said sequence of fluctuation disagreements, said sequence of concentrations and said sequence of times $$I_j = K_0 + K_1 C_j + K_{f1} C_j F_j$$

$$I_j = K_0 + K_1 C_j + K_{f1} C_j F_j + K_{t1} C_j T_j$$

$$I_j = K_0 + K_1 C_j + K_{f1} C_j F_j + K_{t1} C_j T_j + K_{t2} C_j T_j^2$$

wherein the $K_0$, $K_1$, $K_{f1}$, $K_{t1}$ and $K_{t2}$ are coefficients to be regressed out and stored in the computer.

2. A method of eliminating the fluctuation and drift of spectral line intensities with an atomic emission spectrometer or a mass spectrometer including:

measuring the intensities of at least two reference lines and an analytical line for a component in a standard sample j;

correspondingly outputting a time $T_j$ when said standard sample j is measured with a computer which is used to control this spectrometer and store all the measured intensities;

defining an intensity ratio $I_j$ of an analytical line intensity $i_j$ to the first reference line intensity $i_{1j}$ which can be freely selected from one of the intensities of said reference lines for said component in said standard sample j by the following formula;

$$I_j = i_j \div i_{1j}$$

repeating the above measuring, outputting and defining steps until a sequence of standard samples known with a sequence of concentrations $C_j$ are finished to obtain correspondingly a sequence of intensity ratios and a sequence of times wherein j represents one order number of said sequence of standard samples and can be any positive whole number except for zero;

selecting one standard sample s from said sequence of standard samples;

computing a fluctuation disagreement $F_j$ of intensities between said first reference spectral line and a second reference line by the following formula $$F_j = (i_{2j} \div i_{1j}) - (i_{2s} \div i_{1s})$$

wherein $i_{1j}$ and $i_{2j}$ are the intensities of said first and second reference lines, respectively measured for the standard sample j, and $i_{1s}$ and $i_{2s}$ are said first and second reference spectral line intensities, respectively obtained for said selected standard sample s;

repeating the above computing step until a sequence of fluctuation disagreements are obtained correspondingly for said sequence of standard samples; and using an equation to regress out a relationship among said sequence of intensity ratios, said sequence of fluctuation disagreements, said sequence of concentrations and said sequence of times.

3. A method of eliminating the fluctuation of spectral line intensities including:

measuring the intensities of at least two reference lines and an analytical line for a component in a standard sample j;

defining an intensity ratio $I_j$ of an analytical line intensity $i_j$ to the first reference line intensity $i_{1j}$ which can be freely set from one of intensities of said reference lines for said component in said standard sample j by the following formula;

$$I_j = i_j \div i_{1j}$$

repeating the above measuring and defining steps until a sequence of standard samples known with a sequence of concentrations $C_j$ are measured wherein j represents one order number of said sequence of standard samples and can be any positive whole number except for zero;

selecting one standard sample s from said sequence of standard samples;

computing a fluctuation disagreement $F_j$ of intensities between said first reference spectral line and a second reference line by the following formula $$F_j = (i_{2j} \div i_{1j}) - (i_{2s} \div i_{1s})$$

wherein $i_{1j}$ and $i_{2j}$ are the intensities of said first reference line and said second reference line, respectively for the standard sample j, and $i_{1s}$ $i_{1s}$ and $i_{2s}$ are said first and second reference spectral line intensities, respectively obtained for said selected standard sample s;

repeating the above computing step until a sequence of fluctuation disagreements are obtained correspondingly for said sequence of standard samples; and using an equation to determine a relationship among said sequence of intensity ratios, said sequence of fluctuation disagreements, and said sequence of concentrations.

4. A method of eliminating the fluctuation of spectral line intensities including:

measuring the intensities of at least two reference lines and an analytical line for a component in a sequence of standard samples known with a sequence of concentrations;

repeating said measuring step at a sequence of times;

storing the measured intensities resulting from said measuring steps;

calculating the ratios of the intensities of said analytical line to the intensities of a first reference line resulting from said measuring steps;

calculating the ratio of a first sum of at least two of the intensities of a second reference line to a second sum of at least two of the intensities of said first reference line;

computing the differences between the ratios of the intensities of said second reference line to said first reference line and said ratio of said first sum to said second sum; and determining a relationship among said ratios of analytical line intensities to said first reference line intensities, said differences and said concentrations of said component in standard samples.

* * * * *